United States Patent [19]

Morrison

[11] Patent Number: 5,002,890
[45] Date of Patent: Mar. 26, 1991

[54] SPIRAL VANE BIOREACTOR

[75] Inventor: Dennis R. Morrison, Kemah, Tex.

[73] Assignee: The United States of America as represented by the Administrator of the National Aeronautics and Space Administration, Washington, D.C.

[21] Appl. No.: 278,137

[22] Filed: Nov. 29, 1988

[51] Int. Cl.$^5$ .................................. C12M 03/06
[52] U.S. Cl. ................................. 435/286; 435/289; 435/311; 435/315; 435/316; 210/396
[58] Field of Search ................. 435/284–286, 435/289, 291, 311, 313, 316, 818; 210/359, 396

[56] References Cited

U.S. PATENT DOCUMENTS

| | | | |
|---|---|---|---|
| 3,647,632 | 3/1972 | Johnson et al. | 195/142 |
| 3,769,176 | 10/1973 | Hise et al. | 195/142 |
| 4,208,483 | 6/1980 | Lee | 435/284 |
| 4,276,384 | 6/1981 | Mueller | 435/311 |
| 4,286,065 | 8/1981 | Kaluniants et al. | 435/315 |
| 4,289,854 | 9/1981 | Tolbert et al. | 435/286 |
| 4,310,630 | 1/1982 | Girard et al. | 435/284 |
| 4,343,904 | 8/1982 | Birch et al. | 435/240 |
| 4,535,062 | 8/1985 | Muller | 435/289 |
| 4,537,860 | 8/1985 | Tolbert et al. | 435/240 |
| 4,596,779 | 6/1986 | Ono | 435/284 |
| 4,639,422 | 1/1987 | Geimer et al. | 435/286 |
| 4,649,114 | 3/1987 | Mittenburger et al. | 435/286 |
| 4,649,117 | 3/1987 | Familletti | 435/313 |
| 4,649,118 | 3/1987 | Anderson | 435/316 |
| 4,722,902 | 2/1988 | Harm et al. | 435/284 |

FOREIGN PATENT DOCUMENTS 0168379  8/1985  Japan .................. 435/286

OTHER PUBLICATIONS

Lewis et al., "Growth and Maintenance of Anchorage Dependent Cells in Zero Headspace Bioreactor Systems Designed for Microgravity", Proceedings "Spacebound '87", Sep. 14, 1987, pp. 265–268.
Wolf et al., Bioreactor Cell Culture Process (Abstract), Jun. 1988, Acc. #N89-14666.
"The Large-Scale Cultivation of Mammalian Cells", by Joseph Feder & William R. Tolbert, Scientific American, Jan. 1983, vol. 214, No. 1, pp. 36–43.

Primary Examiner—David L. Lacey
Assistant Examiner—William H. Beisner
Attorney, Agent, or Firm—Russell E. Schlorff; Harold W. Adams; Edward K. Fein

[57] ABSTRACT

A spiral vane bioreactor of a perfusion type in which a vertical chamber (10), intended for use in a microgravity condition, has a central rotating filter assembly (30) and has flexible membranes (56) disposed to rotate annularly about the filter assembly. The flexible members have end portions disposed angularly with respect to one another. A fluid replenishment medium is input (68) from a closed loop liquid system to a completely liquid filled chamber containing microcarrier beads, cells and a fluid medium. Output (36) of spent medium is to the closed loop. In the closed loop, the output and input parameters are sensed by sensors (82,96); a manifold 86 permits recharging of the nutrients and pH adjustment; oxygen is supplied and carbon dioxide removed, bubbles are removed and the system is monitored and controlled by a microprocessor (100).

16 Claims, 4 Drawing Sheets

SPIRAL VANE BIOREACTOR

ORIGIN OF THE INVENTION

The invention described herein was made by an employee of the United States Government and may be manufactured and used by or for the Government of the United States of America for governmental purposes without the payment of any royalties thereon or therefor.

RELATED APPLICATIONS

This application has subject matter related to the subject matter disclosed in the commonly assigned U.S. Pat. applications Ser. No. 087,358, filed Aug. 20, 1987, now U.S. Pat. No. 4,839,046, Ser. No. 213,558, filed June 30, 1988, and Ser. No. 213,559, filed June 30, 1988.

FIELD OF THE INVENTION

The present invention relates to an improved spiral vane bioreactor useful for carrying out cell production of mammalian cells particularly in a microgravity environment.

BACKGROUND OF THE INVENTION

Bacterial cell culture processes have been developed for the growth of single cell bacteria, yeast and molds which are encased with a tough cell wall. Mammalian cell culture, however, is much more complex because such cells are more delicate and have a more complex nutrient requirement for development, Large scale culture of bacterial type cells is highly developed and such culture techniques are less demanding and are not as difficult to cultivate as mammalian cells. Bacterial cells can be grown in large volumes of liquid medium and can be vigorously agitated without any significant damage. Mammalian cells, on the other hand, cannot withstand excessive turbulent action without damage to the cells and must be provided with a complex nutrient medium to support growth.

In addition, mammalian cells have other special requirements such that most animal cells must attach themselves to a surface in order to duplicate. On a small scale, mammalian cells have been grown in containers with small microwells to provide surface anchors for the cells. However, the cell culture in microwells generally does not provide sufficient surface area to grow mammalian cells on a large scale basis. To provide greater surface areas, micro-carrier beads have been developed for providing surface areas for the cultured cells to attach. Microcarrier beads with attached culture cells require agitation or movement in a bioreactor vessel to provide suspension of the cells in fresh nutrients. To obtain agitation, such bioreactor vessels have used internal propellers or movable mechanical agitation devices which are motor driven so that the moving parts within a vessel cause agitation in the fluid medium for the suspension of mammalian cells carried on microcarrier beads. However, bioreactor vessels with internal moving parts may damage mammalian cells and also subject the cells to high fluid shearing stresses. If the beads collide with one other, the cells can be damaged.

In summary, bioreactors used to culture mammalian cells typically utilize internal mechanical parts, air, or fluid movement as a lift mechanism to achieve particle suspension. Such mechanisms can induce damage to growing cells or tissues either directly or indirectly by fluid shear.

PRIOR ART

Prior art which is known to applicant includes the following:

U.S. Pat. No. 4,537,860 which relates to a static or stationary system for cell culture of animal cells where the cells in the vessel are supplied with a nutrient 21 which passes through a porous tube 19 into the matrix (with cells) and that exits through passages 24 and 25. Oxygen is passed through a permeable membrane 25.

U.S. Pat. No. 4,310,630 relates to a stationary or static cell culture growth device. In the '630 patent, the patentee proposes to have a rotating cylinder about a horizontal axis which is rotatable between 7 and 20 RPM. Included within the vessel is a matrix of tubular elements 11 for providing increased surface area for growth of cells. Not all of the elements 11 are covered with nutrient and the gas is supplied through one inlet and exited through an outlet.

U.S. Pat. No. 4,343,904 relates to growth of animal cells and a vertical cylindrical vessel having spaced apart plates on an axial shaft. An external pumping loop is provided for circulating the contents of the vessel from the bottom to the top of the vessel. Cell growth is carried out by substantially filling the vessel with cells and growth medium and allowing the cells to settle onto disk surfaces and rotating the shaft while circulating the vessel contents from the bottom to the top for mixing.

U.S. Pat. No. 4,649,117 discloses an air lift bioreactor for maintaining cells in suspension and includes a centrally located gas inlet means at the lower end of the mixing chamber, a conical side wall in the growth chamber and introducing an oxygen containing gas to bubble up through the cells and liquid medium to carry the cells and liquid medium upward from the mixing chamber to the growth chamber and so that the cells and liquid medium flow downwardly along the conical side wall to replace the cells and liquid medium being carried upwards in the mixing chamber. The system is for agitating the cells while minimizing shear forces.

A paper entitled, "The Large Scale Cultivation of Mammalian Cells", by Joseph Feder and William R. Tolbert, published in the Scientific American Magazine, January 1983. Vol. 248, No. 1. pps 36–43. In this paper, agitation of the cells is described as required to keep the cells suspended in the medium and describes a turbine agitator, a marine propeller agitator, and a vibro mixer for mixing. The paper also describes a perfusion reactor in which agitation is provided by four slowly rotating flexible sheets of monofilament nylon which are rotated about a vertical axis while the medium in the main vessel is continuously pumped to the satellite filter vessel. The filter retains the cells which are pumped along with the remainder medium back into the vessel for further proliferation.

The U.S. Pat. No. 3,647,632 shows an apparatus for handling cells in which a centrally located filter is rotated by an external magnetic drive. Fluid and gas are supplied to the mixture for cell growth and fluid is withdrawn from the center of the rotating filter. Samples may be taken of the fluid by an external device and an annularly heating bath is provided for maintaining the temperature of the culture medium. The device does not show the complete enclosure to be filled with fluid. In the Johnson patent the device is rotated about a vertical axis.

In U.S. Pat. No. 4,596,779 a culture vessel has an agitator arranged to orbit about an upright axis. The culture system utilizes microcarrier beads and suspension of the beads in the solution as well as a continuous perfusion culture system which involves removing the media from the culture vessel and supplying fresh medium. In the system agitator 51 orbits but does not rotate. A filter 78 performs functions of agitating and exchange of media between the vessels without stopping movement of the agitator.

U.S. Pat. No. 4,649,118 discloses and relates to the handling of cell cultures for continuously removing expended medium to facilitate cell growth and concentration. The patent illustrates a culture vessel containing a quantity of culture medium with a filter head which is moved in a swinging fashion through the support member through the fluid to create shearing forces about the periphery of the filter 48 to prevent undesirable buildup and clogging of cells and to accomplish such motion a magnetic motor drive is provided.

The U.S. Pat. No. 4,535,062 discloses a fermenting device with a rotary turbine 14 where backflushing of fluid is provided through diaphragm filters and aeriation is provided through an aerating pipe and a distributing member. The filter is not rotated.

U.S. Pat. No. 4,276,384 discloses a fermenter for growing micro-organisms and illustrates a rotary means which is rotatable about a vertical axis. This design uses a rotating turbine 14 at one end of the reactor vessel for agitation in combination with a stationary guide pipe 5 which surrounds the filter pipes 6. The guide pipe serves to direct the fluid flow from one end of the vessel towards the opposite end along the stationary filter pipes. The turbine 14 does not extend along the entire length of the vessel and filters as in the structure of the present invention. The filters in Mueller's design are not mounted coaxially on the same tube or pivot as the turbine. The use of the guide pipe 5 precludes extending their design to this method of using a flexible, spiral vane system mounted coaxially with an independently driven rotating filter, both which extend the entire length of the vessel. Mueller's design also uses gas aeration supplied via conduit 17 and related features to control bubble dispersion and excess foaming by the rotating turbine.

U.S. Pat. No. 3,769,176 discloses and relates to a zero gravity environmental device for the growth of micro-organisms. A closed loop fermentation system has a loop 10 in which fluid is continuously circulated. Cells and substrate are introduced into the loop. Nutrients are introduced into the loop. A dialysis exchanger is used in the loop to return products to the reservoir. In the loop, after fermentation, a membrane removes metabolites. Carbon dioxide is trapped and separated by venting from the system. A sparger provides oxygen into the medium. The system has a cylindrical reactor vessel, dual stirrers, bladder type reservoirs, and filter membranes. However, it does not have capabilities to circulate cell free medium and it was not designed to culture mammalian cells on microcarriers.

U.S. Pat. No. 4,208,483 discloses and relates to a zero gravity device in which a culture medium is passed through a cylindrical chamber containing a plurality of collogen treated discs. The discs are rotated on a shaft.

U.S. Pat. No. 4,286,065 discloses and relates to a vertical vessel where there are perforated partitions and discs and vane type agitators. The vanes illustrated in FIGS. 8,2,12 and 11 are rigid, not flexible. Also, flow gases enter into and out of the culture vessel, therefore, headspace must be provided in the vessel.

Conventional Cell Culture Systems (a) Flasks or Small Static Culture Systems

Basically, standard cultures in culture flasks are not practical under micro-g conditions because the flasks would have to be completely filled with culture medium to avoid uncontrolled exposure of the cells to the gas phase which would cause instant cell rupture. The elimination of the gas headspace, however, is a severe limitation on the ability to dissolve oxygen and exchange $CO_2$. Thus traditional flask type of cultures would only be viable for 24–36 hours.

Small (10–50 ml.) culture chambers with cells attached to a growth surface inside the chamber can be used to maintain confluent cells for a few days. Cells seeded in micro-g could be grown for a few generations if the cells became attached and enough nutrients were available. Periodic changeout of the culture medium would be a major disadvantage to cells which must attach and then grow in micro-g. Skylab showed that hardy cells could be maintained for up to 30 days with periodic medium exchange. However, live cell samples cannot be taken and analyzed during the flight without sacrificing the entire culture in that particular chamber. Growth and repeated medium changeouts of maintenance medium for long term product secretion is impractical in these type systems in current orbital facilities (Shuttle or Spacelab). These systems are best for small scale cell biology experiments and not to investigate cell growth and production of valuable secretory products.

(b) Fixed Matrix Cultures

Culture of cells on hollow fibers, ceramic matrix or embedded in gel matrix systems can be accomplished in micro-g. However, all current designs supply oxygen rich nutrient medium by periodic or continuous flow through from one end of the culture chamber. The $O_2$ (and other nutrient) levels are high at the input end, but rapidly fall off as the medium flows through the vessel. Toxic waste is rapidly removed at the entrance, however, the cells near the exit (downstream) always are exposed to some level of waste from the upstream cells. The cells do not "see" the same nutrient (nor toxic waste) concentrations. As a result cell growth and product efficiencies are not the same throughout the apparatus. In addition, in these systems it is not practical to harvest live cells without stopping the culture and harvesting all cells. Therefore, periodic cell sampling to analyze cell viability and function is not possible.

(c) Suspension Culture Systems

Normal, non-transformed mammalian cells will not grow in free suspension due to their peculiar anchorage dependency. Unanchored mammalian cells do not replicate normally and if denied anchorage to a suitable substrate for more than a 12–24 hours they begin to die and therefore do nor have the opportunity to secrete much useful products.

Encapsulated cells

Cells entrapped in alginate or similar matrix material then suspended in a stirred bio-reactor are somewhat protected from high shear, however, cell numbers within the capsule must be restricted to avoid nutrient starvation and waste toxicity to innermost cells. Although many important fragile human cells and hybridomas cannot be practically grown in these systems on earth, it is not clear that there would be any advantage to using these systems under micro-g.

Microcarriers

Suspended microcarrier bead reactors provide the substrate for cell anchorage and provide a substantial advantage in surface area/medium volume over hollow fibers and ceramic matrix type systems and over standard culture flasks or roller bottles. Microcarriers do sediment in one-g and must be stirred in vat type culture vessels or horizontally rotating clinostats. Comparisons of conventional roller bottle cultures with microcarrier perfusion type bioreactors show that the growth rates are similar, but that the maximum cell density for the perfusion reactor was significantly greater than the conventional cultures. Cell viability was almost 100% in the perfusion reactor system, but only 70% in the conventional system. Cells also can be continuously harvested from the perfusion reactor.

Disadvantages of prior art

Batch or fed-batch cultures are quite limited in the number of cells that can be grown and maintained. Perfusion type culture vessels with spinning filters have been used to grow some anchorage independent cells. However, growth of normal human cells (anchorage dependent) under perfusion conditions must be accomplished in fixed matrix reactors or cells on microcarriers. Fixed matrix reactor vessels do not allow homogeneous distribution of nutrients nor can the shear regimes be carefully controlled to enhance certain cell functions and product secretions. Unique culture systems are required to conduct cell growth experiments in microgravity.

Early development of microcarriers was confined to use in conventional fermentation systems originally designed to culture single cell organisms (yeast, fungi, and bacteria). These systems are not very efficient for sustained culture of mammalian cells and are usually designed to operate in batch or fed-batch modes. Precise control of nutrients and elimination of toxic metabolic wastes was not carefully controlled.

A major problem with conventional bioreactors, designed to use microcarriers, is gravity induced sedimentation of the microcarrier beads. As cell density on the beads increases the sedimentation becomes greater, thus requiring more stirring to keep the beads suspended. Increased stirring results in high shear regimes within the reactor vessel. These high shear levels impart stress to the cells and often tear the cells off of the microcarriers. Cells do not survive long if they remain unattached. Also perfusion type culture operations in very low, favorable shear regimes is quite impractical in conventional systems at one-g.

Limitations of microcarrier cultures appear to be a result of high shear levels generated by stirring methods, bead-to-bead and bead-to-impellor collisions which damage cells and difficulties with gas sparaging required to supply critical oxygen levels. Bubble buoyancy creates foaming problems which in turn reduce cell viability. As cells get carried into the foam they die and release intracellular lysosomes. If only 10% of the cells are lysed the entire batch usually begins to rapidly die. The general limitations on conventional and recently developed microcarrier culture systems appear to directly involve gravity related phenomena such as sedimentation and gaseous bouyancy.

SUMMARY OF THE PRESENT INVENTION

The spiral vane bioreactor of the present invention is embodied in a perfusion type self-contained, closed loop cell culture facility which can operate in microgravity to support cell growth or long term maintenance cultures of fragile mammalian cells or hybridoma cells for process technology experiments or basic cell biology experiments.

This particular culture system of the present invention is designed to: (1) support cell proliferation (exponential growth rates) in complex growth media, and (2) to maintain confluent cells in defined medium under conditions optimized to permit or encourage selected cell functions and secretion of cell products into the culture medium. The system provides continuous environmental control, resupply of oxygen and other critical nutrients as well as removal of toxic metabolic wastes. The bioreactor is controlled by a dedicated microprocessor controller which interfaces with the sensors, transducers and slaved relays and control circuits. This cell culture system is capable of measuring the environment, efficiencies of mass transport, gas transfer rates and is designed to precisely control mechanical stress imposed by mixing or cell/medium separation devices. The basic system is capable of removing and concentrating cell-free culture medium for off-line analysis and product assays. It also has capabilities to interface with the various downstream bioseparation modules which can separate protein products directly from concentrated culture medium effluent streams.

The system basically consists of five major subsystems: (1) A special reaction vessel equipped with a unique coaxial spin filter and flexible stirring vane; (2) a liquid medium circulation loop designed to circulate cell free medium and measure critical dissolved nutrient levels; (3) a product concentration and extraction sideloop; (4) a gaseous exchange system in-line with the main circulation loop; and (5) a built-in microprocessor controller to operate the system automatically.

The culture vessel design uses a spin filter type culture system which allows continuous removal of cell-free medium from the reactor vessel. The mixing and spinning filter functions are uncoupled by using separate motors, magnetic drives and coaxial mounting on a hollow shaft which allows independent control of the spin filter (and therefore the medium withdrawal rate) and the stirring device.

The co-axial spin filter with flexible, hydrodynamically contoured, vanes positioned strategically between the spin filter and the vessel wall (to minimize turbulence and high shear fields) is designed to operate within an optimum range of rotation rates to create uniform mixing, suspend the cells or microcarriers, and minimize the shear or collision trauma to the cells. The coaxial configuration allows for high spin rates of the filter needed to allow medium withdrawal from the reactor vessel at high flow rates (80–110 ml./min.) and slow, independent rotation of the stirring vanes to provide convection (mixing) flow cells within the vessel. Independent motors driving the spinning filter and the stirrer vanes also allows a wide range of r.p.m.'s for the stirrer and more precise control of the shear regimes that the cells are exposed to in the reactor vessel.

The main fluid loop connects the reactor vessel, sensor blocks, filtrate manifold, hollow fiber - dialysis refeed subsystem, gas exchange module (oxygenator) and the protein concentration sideloop. The position of the sensor blocks which allows the microprocessor to calculate cell metabolic rates from the difference in dissolved oxygen and carbon dioxide levels in the input and the outflow from the reaction vessel. Reservoir vessels are connected by conduit and valves to allow for automatic addition of concentrated culture medium, acid or base for pH control. The hollow fiber dialysis system is independently controlled with its own circulation pump. Concentrated make-up medium is circulated in this sideloop between the medium reservoir and the hollow fiber cannister. Concentrated nutrients are transported by dialysis through the fibers into the main medium stream (the reservoir also can act as a repository for accumulating metabolic wastes).

The gas exchange system consists of a semi-permeable membrane (or hollow fiber) gas exchange or "oxygenator" module which provides for transport of oxygen through the membrane to saturate the depleted culture medium and at the same time provides removal of carbon dioxide from the main loop. This module consists of two chambers separated by the gas permeable membrane and operates similar to a conventional "blood oxygenator". Culture medium flows through one compartment while pressure regulated gas flows through the other. The gas supply consists of high pressure oxygen or custom mixed gas containers, flow and pressure regulators, and is controlled by the microprocessor. The subsystem can be operated either as a closedloop or a bleed-gas type system and is controlled to maintain critical levels of oxygen and carbon dioxide by volume gas flow or percentage gas mixing in correlation with the existing medium flow rate and the metabolic requirements of the cells.

A microgravity bubble trap has also been included to remove any bubbles formed by gas dissolution during temperature or pressure changes and to trap any gas bubbles which may be injected into the medium circulation loop should the oxygenator membrane develop a leak during operations in micro-g conditions.

The function of the high molecular weight filter loop is to remove serum proteins from growth medium before changeout to maintenance medium when cells are confluent and to periodically (every 3 or 4 days) concentrate a sample of the circulating medium for product assays. This loop consists of a diaphragm reservoir, a circulation pump, a high molecular weight (HMW) ultrafilter and connections for low molecular weight (LMW) filtrate to be delivered to a waste reservoir or returned to the main medium circulation loop. Isolation valves and a movable diaphragm or piston in the sample reservoir allows the volume of the concentrate to be reduced as the LMW filtrate is removed.

The microprocessor control system is a system designed to automatically control the bioreactor to set point values, log sensor data, display status and provide alert or alarm functions. The microprocessor operates using multi-tasking Basic, turbo Pascal or Forth programming languages. It includes sensors for dissolved oxygen, $CO_2$ pH, $NH_4$, redox potentials and other chemicals dissolved in the culture medium. The main process controller can status and/or reprogram slaved microprocessor control cards which control independent flow loops for gas exchange and other functions. The system includes the capability to interface with various personal computers which in turn can operate off-line to perform statistical analysis of data, and predict adverse trend interception with alert or alarm set points. The process controller also has the capability to be updated with software commands from a "supervisory computer"

Cells cultured in weightlessness or microgravity will not sediment. Thus, the only stirring required is to distribute oxygen and nutrients to the cells. The amount of stirring is considerably less than 1-g which means less turbulence and lower rates of cell death. There is no headspace in the housing, i.e. the fluid completely fills the chamber. The temperature of the system is preferably at $37° \pm 1°$ C. The flow rate is 20 to 100 ml/minute.

DESCRIPTION OF THE PRESENT INVENTION

Figure 1:
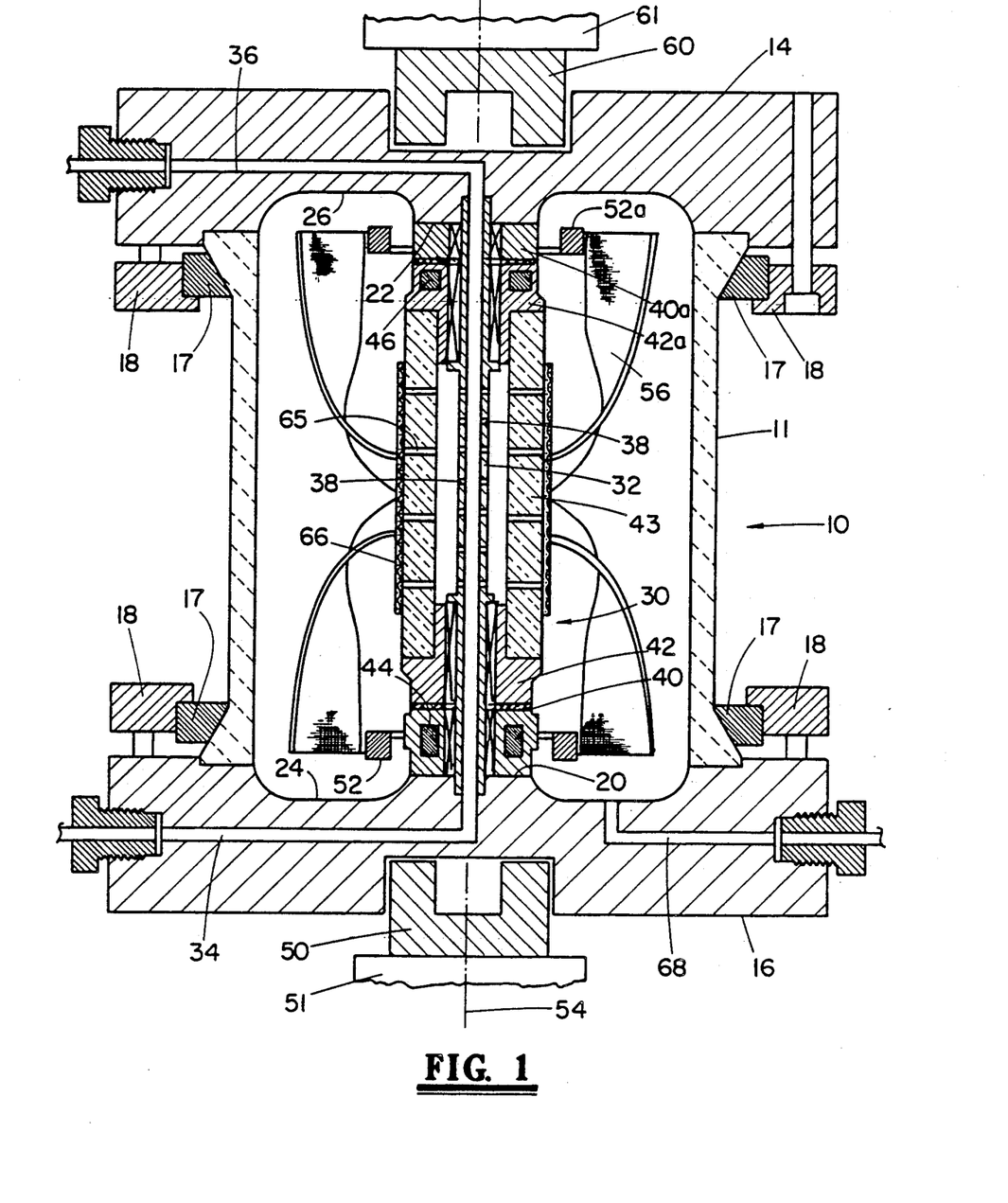
FIG. 1 is a schematic view in cross-section through a Bioreactor Vessel.

Referring now to FIG. 1, the bioreactor or reaction vessel 10 includes an elongated, upright, tubular outer housing member 11 constructed of glass or plastic. The annular end surfaces of the housing member 11 interfit with and engage cylindrically shaped flat surfaces on upper and lower end members 14 and 16. The upper and lower end members 14, 16 are constructed of metal such as non-magnetic stainless steel. Segmental clamp members 17 are arranged about the circumference of outwardly flared terminal ends on the housing member 11 and annular clamp rings 18 are bolted to the end members 14 and 16. The clamp rings 18 bear upon the segmental clamp members 17 to provide a tightly sealed joint and interconnection between the end members 14, 16 and the housing member 11. Each end member 14 and 16 has a central cylindrically shaped internal pedestal 20 and 22 coaxially disposed within the housing member 11. Located around each central pedestal 20 and 22 is an annular groove 24 and 26 where each groove defines smooth curves between an annular bottom surface and the outer wall of the housing member 11 and between the pedestal 20 and the pedestal 22.

A central filter assembly 30 includes a central tubular pipe or tube member 32 extending along a central axis for the pedestals 20, 22 and coupling to flow passages 34, 36 in the upper and lower end members 14 and 16. The tubular member 32 has flow passages or openings 38 disposed along its length for liquid access. At each end of the tubular member 32 are first annular support members 40,40a and second annular support members 42,42a. The support members 40,40a,42,42a are mounted for rotation on the central tubular member 32 by suitable bearing means. The lower first support member 40 has implanted magnetic elements 44 while the upper second support member 42a has implanted magnetic elements 46. Between the second support members 42,42a is a tubular ceramic member 43. The lower end member 16 has a cylindrical recess 48 located in axial alignment with the pedestal 20 on the lower end member 16. A magnetic drive member 50 and drive means 51 are located relative to the recess 48 so that a magnetic coupling is created with the magnetic elements 44. The drive means 51 thus rotates the first support member 40 within the housing member 11. Magnetic drive means shown in U.S. Pat. No. 4,836,826 may be utilized.

The first support members 40,40a are each provided with a minimum of four equiangularly spaced, arm members 52,52a. The arm members 52,52a extend radially outward and transverse to a central axis 54 for the filter assembly 30. Flexible membrane members 56 are connected between an upper arm member 52a and a lower arm member 52 (where the lower arm member 52 is displaced 90° angularly from the upper member). The four flexible membrane members 56 may be made of nylon and are strips of material which are stiff enough so that rotation of the first lower member 40 will cause a corresponding rotation of the first upper member 40a.

Figure 5:
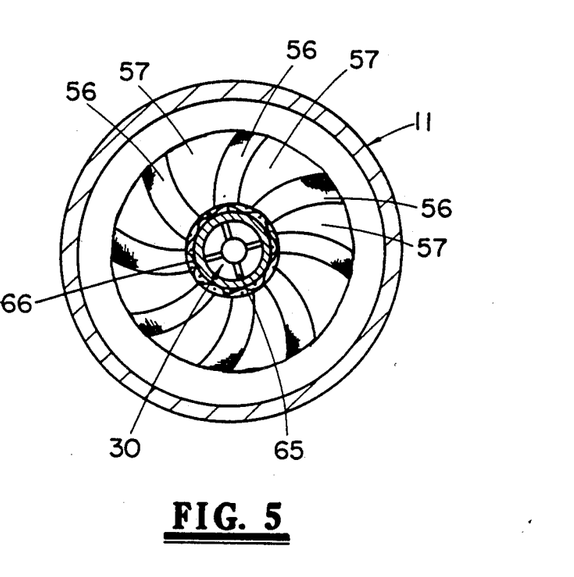
FIG. 5 is a view similar to FIG. 4 but showing an alternate configuration.

If desired, the number of arm members 52,52a and flexible membrane members can be increased to 12 members. Also, it may be preferable to use a disc member 57 instead of arm members which would reduce the agitation factor. (See FIG. 5).

The upper second member 42a is driven by a magnet drive member 60 and motor means 61 which are independent of the lower drive member 50 and drive means 51. Between the upper second support member 42a and the lower support member 42, the tubular filter cylinder 43 constructed of ceramic material and has access ports 65 extending through its walls. A porous membrane 66 covers the length of the cylinder 43 and prevents microbeads from passing through the cylinder access ports 65. The independent upper and lower drive means 51,61 permit the cylinder 43 to be rotated by the second members 42,42a independently of the rotation of the flexible strip members 56 attached to the first members 40,40a. The rotation of these two mechanisms can be independent of one another and can be simultaneously in the same direction, or in opposite directions or at different speeds, as desired. An inflow passageway 68 is located in the lower end member 16 and opens to a lower end surface for the annular chamber within the housing member 11.

From the above structure, it can be appreciated that fresh nutrients can be input to the interior of the housing member 11 via an inflow passageway 68. In the interior of the housing member 11, microcarrier beads and mammalian cells can be kept in suspension by rotation of the membrane members 56. The membrane members have a width approximately equal to one half of the annulus spacing between the housing member 11 and the cylinder 43. The length to diameter ratio for the interior of the housing member 11 is about 3 to 1 for the velocity range of fluid flow. The cylinder 43 can be rotated as desired for preventing buildup on the membrane 66. Spent nutrients exit through the membrane and the cylinder 43 to the central pipe member 32 and the outflow passages 34, 36.

Figure 4:
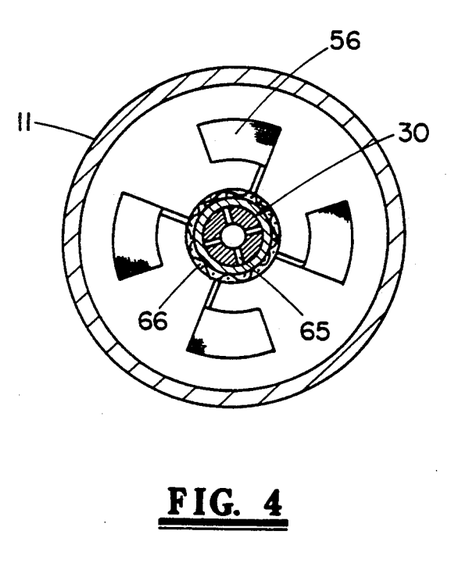
FIG. 4 is a schematic view in cross-section taken midway of the length of the housing member 11 to illustrate flow.

As shown schematically in FIGS. 1 and 4, there are four flexible members 56 which are suspended axially between the upper and lower sets of axial spokes or rods 52,52A. The flexible members 56 when rotated relative to the filter assembly 30 creates a smooth hydrodynamic flow of liquid over the exterior surface of the flexible members which is faster than the flow of liquid over the interior surface of the flexible members. The differential flow creates a lift vector (like a hydrofoil) perpendicular to the flexible members that moves the microcarrier beads tangentially away from the higher shear field near the filter. Thus, a vertical convection flow of cells is created within the housing member 11 while creating only a minimum amount of turbulence and induced shear outwardly along the radius of the housing member 11. With the housing member 11 having a fixed wall, some shear is created at the boundary layer of medium nearest the vessel wall, however, the vertical convection will tend to minimize the residence time of the microcarriers in the higher shear field near the wall of the housing member 11.

Figure 2:
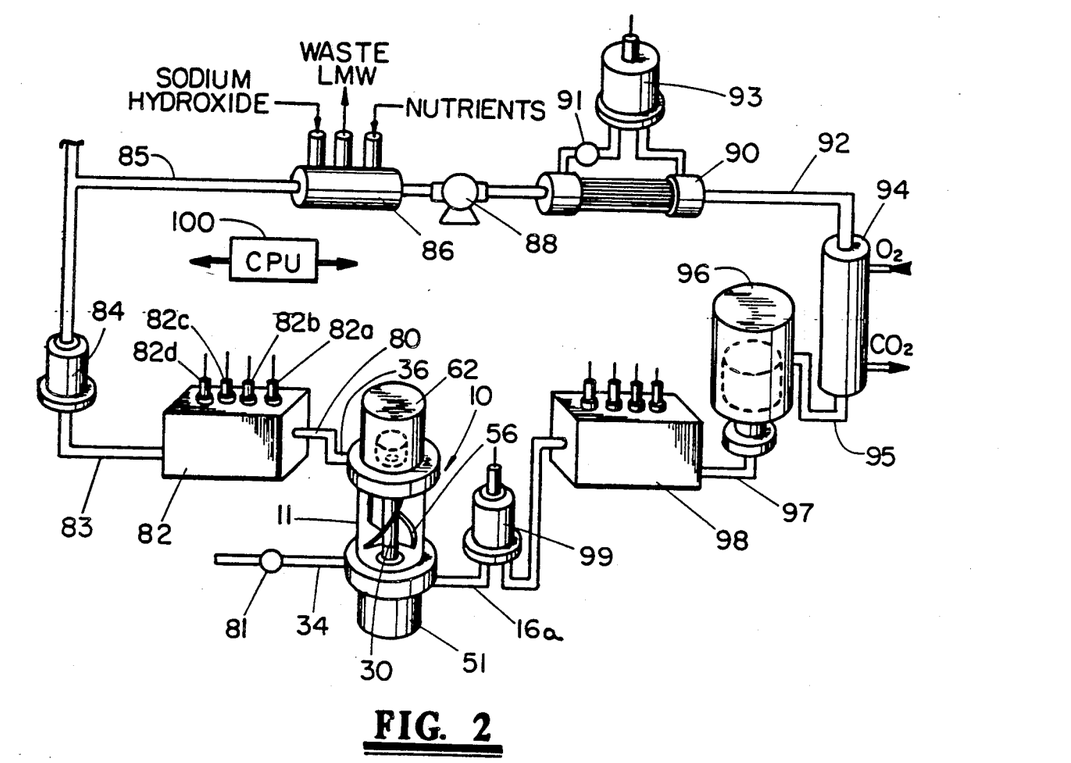
FIG. 2 is a schematic representation of the main loop in a process system using the Bioreactor Vessel.

Referring now to FIG. 2, in the main fluid loop, the outflow conduit 36 in the reactor vessel 10 is coupled by a conduit 80 to a sensor block 82. The other outflow conduit 34 is coupled to a sample valve 81 for withdrawing samples, as desired. The output of the sensor block 82 is coupled by a conduit 83 to a filter means 84. The output of the filter means 84 is connected by a conduit 85 to a filtrate manifold 86. The output of the manifold 86 is coupled by conduit and a pump 88 to a hollow fiber-dialysis refeed subsystem 90. The refeed system 90 is connected by a conduit 92b to a gas exchange module (oxygenator) 94. The oxygenator 94 is connected by a conduit 95 to a bubble trap means 96. The bubble trap means 96 is connected by a conduit 97 to input sensor block 98. The sensor block 98 is coupled to the input of the vessel 10 via a pressure control means 99. All of the various units are interconnected to a CPU microprocessor 100 for control of the system. The microprocessor 100 calculates cell metabolic rates from the difference in dissolved oxygen and carbon dioxide levels in the input and the outflow from the reaction vessel as well as control the flow in the process.

As schematically illustrated in FIG. 2, the reactor vessel 10 includes the upright tubular housing member 11, the central rotatable filter assembly 30, and an an intermediate vane assembly consisting of spiral flex members 56. The spiral flex members 56 can be rotated about the vertical central axis of the housing member in the annulus between the filter assembly and the housing member by the drive means 51. The drive means 62 is used to rotate the filter assembly 30.

Within the housing member 11 are microbead carriers together with mammalian cells to be grown and a liquid nutrient which completely fills the housing (zero headspace). Fresh nutrient is supplied into the housing member via the input passageway 16 where rotation of the flex members 56 maintains the microbeads and attached cells in suspension in the liquid medium. Spent or depleted nutrient is outflowed through the filter assembly 30 in the housing member through the outflow passageway 36. The outflow passageway 36 couples to the sensor block means 82 which detects the levels of oxygen, carbon dioxide, and the pH value as well as the reduction-oxygen potential in the spend nutrient fluid. The sensor block means 82 consists of a Delrin block with a through channel and electrochemical sensors 82 (a-d) for sensing the various parameters of the nutrient. From the sensor block means 82, the output flow is sent through a filter 84 which removes any debris or particulate matter which may have gotten into the system. From the filter 84, the main flow is through a flow conduit 84 to a filtrate manifold 86. In the manifold concentrated medium or sodium hydroxide may be added as necessary and low molecular waste products can be shunted out. The output from the filtrate manifold 86 is connected to the main pump 88 which outputs a flow of liquid to a hollow fiber flow member 90. The flow member 90 has a bypass loop including a pump 91 and a dialysis unit 93 to separate out wastes.

The outflow from the hollow fiber member 90 passes to an oxygenator means 94 where nitrogen and oxygen are passed through a membrane while carbon dioxide passes from the medium to the gas mixture. The oxygenator has a membrane that is permeable to oxygen and carbon dioxide. The outflow from the oxygenator 96 is connected to a bubble trap means which removes any bubbles from the system. Bubbles can be formed by gas dissolution during pressure or temperature changes. The liquid outflow from the bubble trap means 96 connects to an input sensor block which detects the level of oxygen, dissolved carbon dioxide and pH potential as well as the reductionoxidation value. From the sensor block 98, the output goes to a pressure control device 99 and is then input to the reactor vessel 10.

Thus, there is a closed loop system in which both the input and output flows to the bioreactor vessel are sensed for the proper levels of the constituent parameters in the liquid flow so that any adjustment required can be made in the input of a constituent parameters to the liquid. This control and adjustment may be manual or by the computer 100.

Figure 3:
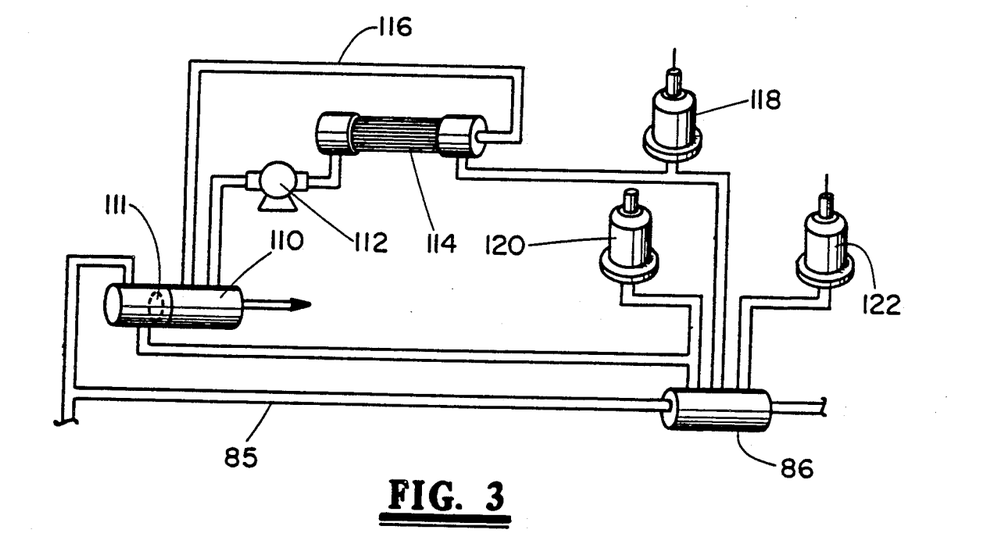
FIG. 3 is a schematic representation of a side loop of the process system.

Referring now to FIG. 3, a recycling loop is connected to the conduit 85 from the filter 84. The input from the conduit 84 is to a manifold or mixer means 110 containing a movable wall diaphragm 111. The diaphragm 111 serves as a buffer and as a reservoir between the relatively low flow main loop system and a higher flow in the recycling loop. In the recycling loop, a pump means 112 provides a flow of liquid to a high molecular weight ultra filter unit 114. Eighty to ninety percent of the media passing through the filter unit 114 is shunted back by a conduit 116 to the mixer 110 while the remaining percent is bled off as waste to a low molecular waste collector 118. A source 120 of sodium hydroxide is connected to the manifold 86. A source 122 of fresh nutrient is also connected to the manifold 86.

The function of the high molecular weight filter loop 110 is to remove serum proteins from growth medium before changeout to maintenance (serum-free) medium when cells are confluent and to periodically (every 3 or 4 days) concentrate a sample of the circulating medium for product extraction and assays. This loop consists of a diaphragm reservoir 110 illustrated in FIG. 3, a circulation pump 112, a high molecular weight (HMW) ultrafilter 114 and connections for low molecular weight 118 (LMW) filtrate to be delivered to a waste reservoir or returned to the main medium circulation loop. Isolation valves (not shown) and the diaphragm 111 in the sample reservoir allow the volume of the concentrate to be reduced as the LMW filtrate is removed.

The gas exchange system or oxygenator 94 consists of a semi-permeable membrane (or hollow fiber) gas exchange or "oxygenator" module which provides for transport of oxygen through the membrane to saturate the depleted culture medium and at the same time provides removal of carbon dioxide from the main loop. This module consists of two chambers separated by the gas permeable membrane and operates similar to a conventional "blood oxygenator". Culture medium flows through one compartment while pressure regulated gas flows through the other. The gas supply consists of high pressure oxygen or custom mixed gas containers, flow and pressure regulators, and is controlled by the microprocessor. The subsystem can be operated either as a closed-loop or a bleed-gas type system and is controlled to maintain critical levels of oxygen and carbon dioxide by volume gas flow or percentage gas mixing in correlation with the existing medium flow race and the metabolic requirements of the cells.

The microprocessor control system 100 is a system designed to automatically control the bioreactor vessel 11 to set point values of the parameters, log sensor data, display status and provide alert or alarm functions. The microprocessor 100 can operate using multi-tasking Basic, turbo Pascal or Forth programming languages. The microprocess control system 100 can status and/or reprogram other slaved microprocessor control cards which control independent flow loops for gas exchange and other functions.

Figure 6:
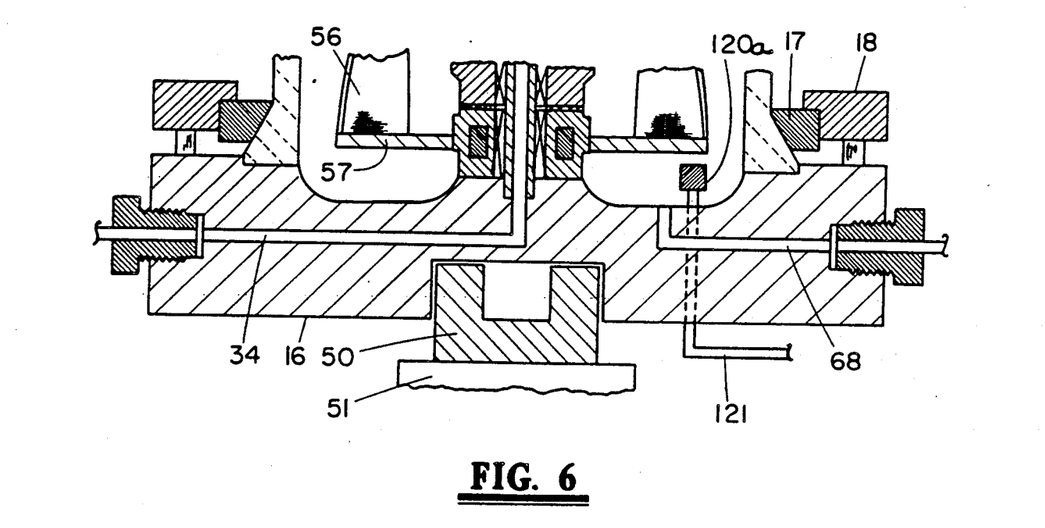
FIG. 6 is a partial view similar to FIG. 1 and showing an alternate arrangement.

Referring now to FIG. 6, an alternative embodiment is shown with the disc support 57 for the flexible members 56. In addition, in the alternate form, a sparger 120a is located within the culture vessel The sparger 120a can be constructed from sintered glass and is used for dispersing oxygen bubbles or fluorocarbon oxygen carrier fluid bubbles into the medium. An input conduit 121 is connected to a source for the input bubbles within the vessel chamber, the medium completely fills the chamber (zero headspace) with the microcarrier beads and cells. The separate input of oxygen increases the oxygen input to the cells which remain dispersed throughout the liquid phase. Removal of the bubbles can be controlled by the speed of rotation of the filter assembly 30. When a fluorocarbon or other type of oxygen carrying chemical is utilized, it is possible to not only supply additional oxygen to the medium but also to transport carbon dioxide out of the culture medium. In utilizing this system the bubble trap means 96 is still used because the introduction of bubbles is controlled by the sparger 120a.

Figure 7:
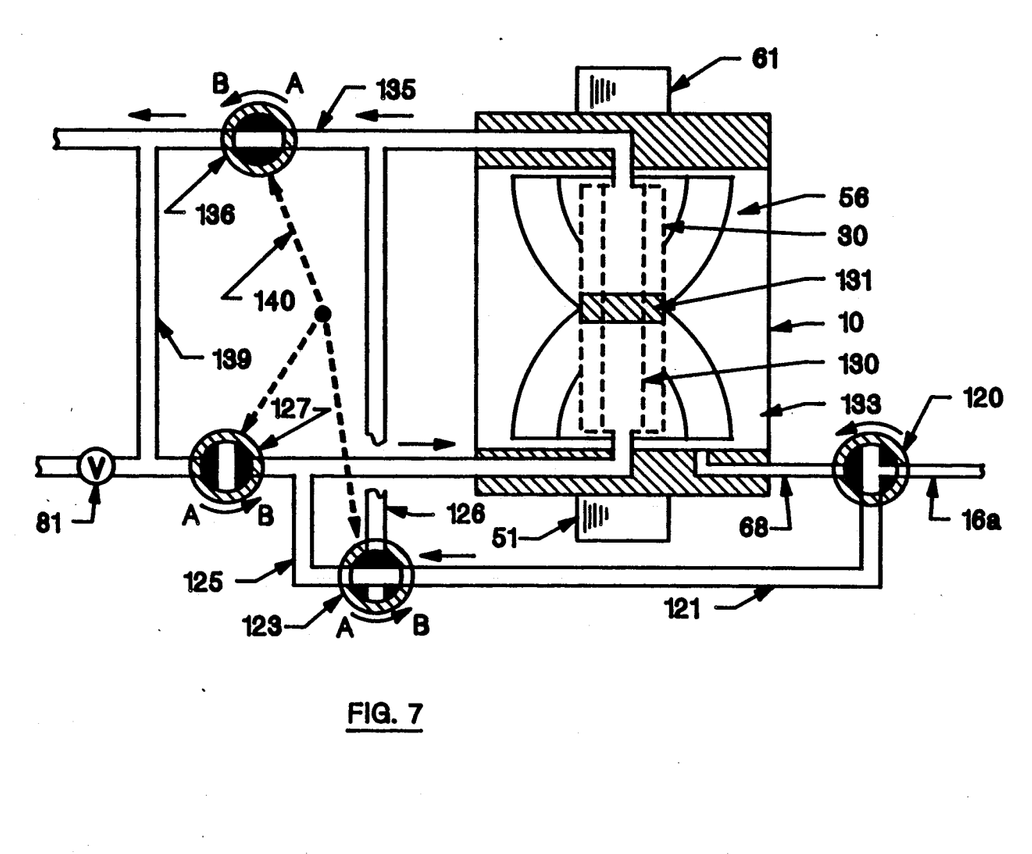
FIG. 7 is a schematic representation of an alternative form of the invention.

Referring now to FIG. 7, a spiral vane bioreactor 10 has a rotating central filter assembly 30 and an intermediate rotating vane system 56. An input line 16a has a valve 119 which is rotatably movable between the position coupling the input flow to the conduit 68 and a position coupling the input flow to a bypass conduit 124. The bypass conduit 124 is coupled by a valve 123 which is rotatable to selectively couple the conduit 124 to a conduit 125 or a conduit 126. The conduit 125 is coupled to a valve 127 and to a vessel conduit 128. In the position shown for the valve 123 and the valve 127, the liquid flow is into a center pipe 130 in the filter assembly 30. Midway of the center pipe 130 and the filter assembly 30 is a barrier 131 which confines the input of liquid through perforations in the lower one-half center pipe 130 and the membrane (not shown). Output of liquid from the chamber 133 in the bioreactor 10 is to the upper one-half of the center pipe 130 (above the barrier 131) and out through a conduit 135, through an open valve 136 to a conduit for the loop system previously described.

Figure 8:
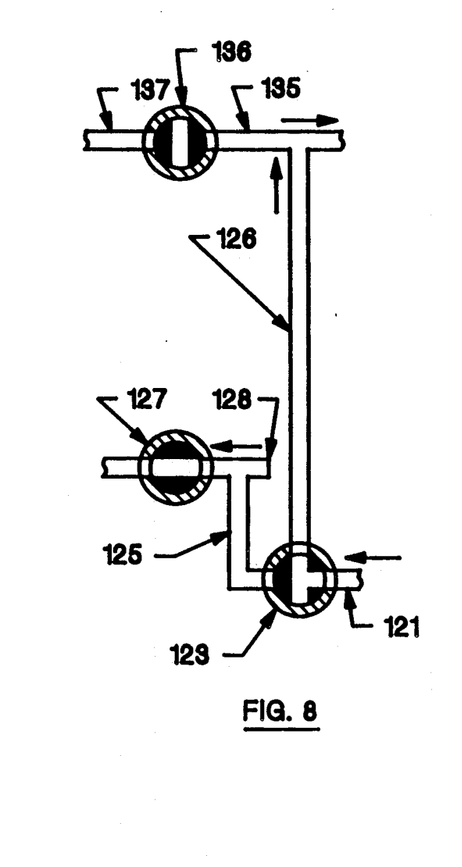
FIG. 8 is a partial view of the valves of FIG. 7 in a different position.

In a second operating condition, the valves 123, 127 and 136 are rotated from an A to a B position. In the B position of the valves 123, 127 and 136 (see FIG. 8A), the input liquid is supplied to the conduit 126 and to the upper one-half of the center pipe 130. Output flow from the lower one-half of the center pipe 130 flows through the conduit 128, the valve 127 and the conduit 139 to the output conduit 137.

By use of a common control (shown by the dashed line 140), the valves 123, 127 and 136 may be operated to alternately apply the fluid flow to the bottom and to the top one-half of the center pipe 130. This alternately reverses the flow through the filter membrane 66 and provides a continuous backflush of the membrane for preventing clogging.

It will be apparent to those skilled in the art that various changes may be made in the invention without departing from the spirit and scope thereof and therefore the invention is not limited by that which is enclosed in the drawings and specifications but only as indicated in the appended claims.

I claim:

1. A bioreactor for use in a closed loop cell culture system under microgravity conditions for maintenance and growth of mammalian cells in suspension in a liquid environment while changing nutrients, said bioreactor including:
   an elongated, stationary, upright, tubular culture vessel containing a nutrient liquid, microcarrier beads, and mammalian cells completely filling the culture vessel;
   end cap means enclosing the ends of said culture vessel;
   rotatable tubular filter means co-axially disposed in said culture vessel and extending between said end cap means so as to define an annular culture chamber between said tubular filter means and the inner wall of the vessel;
   said filter means including a tubular membrane disposed over a perforated tubular member between said end cap means, said perforations providing flow communication between an interior of said tubular member and said tubular membrane, said tubular membrane being permeable to liquids within said culture chamber but non-permeable with respect to the microcarrier beads;
   means for admitting an input liquid containing fresh nutrients and oxygen to said culture chamber at one end of said culture vessel and means for exiting liquid from said culture vessel in communication with said interior of said tubular member;
   flexible strip members disposed in said culture chamber lengthwise of said culture vessel and located between said filter means and the inner wall of said culture vessel;
   rotatable support means rotatably supporting said strip members and located at said end cap means for said culture vessel, wherein the opposite ends of said strip members are connected to said support means at an angular displacement with respect to the longitudinal axis of the culture vessel, and said strip members comprise spiral vanes which when rotated create lift vectors that move the microcarrier beads tangentially away from the high shear field near the filter means; and
   drive means for rotating said filter means and said support means independently of one another about the longitudinal axis of the culture vessel.

2. The bioreactor as set forth in claim 1 wherein the annular culture chamber has a defined first width and said flexible strip members have a second width approximately equal to one-half of the first width.

3. The bioreactor as set forth in claim 2 wherein said drive means are externally located magnets which couple to magnetic elements respectively in the filter means and the support means.

4. The bioreactor as set forth in claim 2 wherein said support means includes radial spoke members.

5. The bioreactor as set forth in claim 2 wherein said support means includes disc members.

6. The bioreactor as set forth in claim 4 wherein there are at least four of said flexible strip members.

7. The bioreactor as set forth in claim 5 wherein there are at least four of said flexible strip members.

8. The bioreactor as set forth in claim 1 and further including a closed loop liquid flow system, which is in flow communication with said means for admitting an input liquid and said means for exiting liquid, for extracting spent liquid nutrient from the culture vessel and for processing and resupplying fresh liquid nutrient and oxygen to the culture vessel, said system including input sensor means and output sensor means positioned and arranged so as to detect various chemical parameters of the liquid in the system, wherein said various chemical parameters are selected from the group consisting of oxygen concentration, carbon dioxide concentration, pH, and reduction-oxidation potential, said input sensor means being adjacent said means for admitting an input liquid and said output sensor means being adjacent said means for exiting liquid, and pump means for recirculating liquid through the system.

9. The bioreactor as set forth in claim 8 and further including an oxygenator means disposed in said system at least between said input sensor means and said output sensor means.

10. The bioreactor as set forth in claim 9 and further including a dialysis means disposed in said system at least between said input sensor means and said output sensor means.

11. The bioreactor as set forth in claim 10 and further including microprocessor means connected to said input sensor means and said output sensor means and at least one of said pump means, oxygenator means, and dialysis means so as to control at least one of said pump means, oxygenator means, and dialysis means in response to signals generated by said input and output sensor means.

12. The bioreactor as set forth in claim 10 and further including a bubble extractor disposed in said system at least between said oxygenator means and said input sensing means.

13. The bioreactor as set forth in claim 1 and further including sparger means disposed in said culture vessel so as to provide flow communication between said annular culture chamber and an exterior gas source.

14. A bioreactor for use in a closed loop cell culture system under microgravity conditions for maintenance and growth of mammalian cells in suspension in a liquid environment while changing nutrients, said bioreactor including;
   an elongated, stationary, upright, tubular culture vessel containing a nutrient liquid, microcarrier beads, and mammalian cells completely filling the culture vessel;
   end cap means enclosing the ends of said culture vessel;
   rotatable tubular filter means co-axially disposed in said culture vessel and extending between said end cap means so as to define an annular culture chamber between said tubular filter means and the inner wall of the vessel;

said filter means including a tubular membrane disposed over a perforated tubular member between said end cap means and barrier means disposed in said tubular member so as to define two separate interior sections, said perforations providing flow communication between an interior of said tubular member and said tubular membrane, said tubular membrane being permeable to liquids within said culture chamber but non-permeable with respect to the microcarrier beads;

means for admitting an input liquid containing fresh nutrients and oxygen to said culture vessel in flow communication with one of said interior sections of said tubular member and means for exiting liquid from said culture vessel in flow communication with the other of said interior sections of said tubular member;

means for rapidly alternating the communication of said means for admitting an input liquid and said means for exiting liquid with said interior sections so as to provide an effectively continuous backflush of the tubular member and membrane thereby preventing clogging without major alteration of the flow patterns within the vessel;

flexible strip members disposed in said culture chamber lengthwise of said culture vessel and located between said filter means and the inner wall of said culture vessel;

rotatable support means rotatably supporting said strip members and located at said end cap means for said culture vessel, wherein the opposite ends of said strip members are connected to said support means at an angular displacement with respect to the longitudinal axis of the culture vessel, and said strip members comprise spiral vanes which when rotated create lift vectors that move the microcarrier beads tangentially away from the high shear field near the filter means; and drive means for rotating said filter means and said support means independently of one another about the longitudinal axis of the culture vessel.

15. A closed loop system for growing mammalian cells in a microgravity environment, said system including;

an elongated, stationary, upright, tubular culture vessel containing a nutrient liquid, microcarrier beads, and mammalian cells completely filling the culture vessel;

end cap means enclosing the ends of said culture vessel;

rotatable tubular filter means co-axially disposed in said culture vessel and extending between said end cap means so as to define an annular culture chamber between said tubular filter means and the inner wall of the vessel;

said filter means including a tubular membrane disposed over a perforated tubular member between said end cap means, said perforations providing flow communication between an interior of said tubular member and said tubular membrane, said tubular membrane being permeable to liquids within said culture chamber but non-permeable with respect to the microcarrier beads;

means for admitting an input liquid containing fresh nutrients and oxygen to said culture chamber at one end of said culture vessel and means for exiting liquid from said culture vessel in communication with said interior of said tubular member;

flexible strip members disposed in said culture chamber lengthwise of said culture vessel and located between said filter means and the inner wall of said culture vessel;

rotatable support means rotatably supporting said strip members and located at said end cap means for said culture vessel, wherein the opposite ends of said strip members are connected to said support means at an angular displacement with respect to the longitudinal axis of the culture vessel, and said strip members comprise spiral vanes which when rotated create lift vectors that move the microcarrier beads tangentially away from the high shear field near the filter means;

drive means for rotating said filter means and said support means independently of one another about the longitudinal axis of the culture vessel;

a main fluid circulation loop for receiving cell-free nutrient liquid from the culture vessel in flow communication with said means for admitting an input liquid and said means for exiting liquid, said loop including pump means positioned so as to provide liquid circulation, pressure regulator means positioned and arranged so as to control pressure differences between said circulation loop and said culture vessel, outflow sensor block means and inflow sensor block means positioned and arranged so as to detect various chemical parameters of the liquid, wherein said various chemical parameters are selected from the group consisting of oxygen concentration, carbon dioxide concentration, pH, and reduction-oxidation potential, said outflow sensor block being adjacent said means for exiting liquid, said inflow sensor block being adjacent said means for admitting an input liquid, a first manifold means constructed and arranged so as to provide for the addition of nutrients and acid or base fluids of pH adjustments to the liquid, dialysis means constructed and arranged so as to separate wastes from the liquid, semi-permeable membrane-type gas exchange means positioned and arranged so as to provide oxygen and removal of at least carbon dioxide or ammonia gases, said first manifold means, said dialysis means and said gas exchange means all being disposed at least between said outflow sensor block means and said inflow sensor block means, microgravity bubble trap means for elimination of free gas bubbles from the liquid, said bubble trap means disposed at least between said gas exchange means and said inflow sensor block means; and microprocessor means connected to said inflow sensor block means and said outflow sensor block means and at least one of said pump means, said first manifold means, said dialysis means, and said gas exchange means so as to control at least one of said pump means, said first manifold means, said dialysis means, and said gas exchange means in response to signals generated by said inflow and outflow sensor block means.

16. The closed loop system of claim 15, which further includes a product concentrating and extraction side loop disposed at least between said first manifold means and said outflow sensor block means, said side loop including:

a second manifold means having a movable wall diaphragm constructed and arranged so as to allow concentrated liquid to be removed from said main fluid circulation loop without altering the pressure in said main fluid circulation loop;

circulation pump means positioned so as to provide liquid circulation within said side loop; and high molecular weight ultrafilter means constructed and arranged so as to return concentrated liquid to said second manifold means and to return low molecular weight filtrate to at least said first manifold means.

* * * * *